United States Patent [19]

Guodong

[11] Patent Number: 5,543,407
[45] Date of Patent: Aug. 6, 1996

[54] PREPARATION AND APPLICATION OF SCOPOLAMINE AND CHLORPROMAZINE AS A DRUG-WITHDRAWAL AGENT

[75] Inventor: Yang Guodong, Ningbo, China

[73] Assignee: Ningbo Institute of Microcirculation and Henbane, ZheJiang Province, China

[21] Appl. No.: 112,417

[22] Filed: Aug. 26, 1993

[30] Foreign Application Priority Data

Sep. 30, 1992 [CN] China ................................. 92111274.2

[51] Int. Cl.⁶ ......................... A61K 31/54; A61K 31/40; A61K 31/44
[52] U.S. Cl. ...................... 514/226.2; 514/411; 514/291
[58] Field of Search ..................... 514/810, 811, 514/812, 813, 291, 223, 304, 557; 424/10

[56] References Cited

U.S. PATENT DOCUMENTS

| | | | |
|---|---|---|---|
| 4,555,397 | 11/1985 | Bachynsky | 424/10 |
| 4,746,509 | 5/1988 | Haggiage et al. | 424/449 |
| 5,034,400 | 7/1991 | Olney | 514/315 |
| 5,189,064 | 2/1993 | Blum et al. | 514/561 |

OTHER PUBLICATIONS

Chlorpromazine and Scopolamine in USP XXII, p. 293–294 and 1238–1239 (1990).
O'Brien, "Drug Abuse and Dependent", *Cecil Textbook of Medicine*, 19th ed., 47–55 (1992).
Weiner, "Atropine, Scopolamine, and Related Antimuscarinic Drugs", *The Pharmacological Basis of Therapeutics*, 6th ed., Goodman and Gilman Ed., 120–132, Chapter 7 (1980).
Gold et al., "Clonidine Blocks Acute Opiate–Withdrawal Symptoms", *The Lancet*, 599–601 (1978).

*Primary Examiner*—Theodore J. Criares
*Attorney, Agent, or Firm*—Merchant, Gould, Smith, Edell, Welter & Schmidt, P.A.

[57] ABSTRACT

An empirical efficacy appears in the drug-withdrawal treatment of drug dependence with a novel drug-withdrawal scopolamine agent(DSA) which contains scopolamine hydrobromide as a subsidiary component. Each of the drugs may be used either combined as an injectable preparation or used integrately as separated injections for drug-withdrawal treatment.

17 Claims, No Drawings

PREPARATION AND APPLICATION OF SCOPOLAMINE AND CHLORPROMAZINE AS A DRUG-WITHDRAWAL AGENT

BACKGROUND OF THE INVENTION

I. Field of the Invention

This invention concerns mainly a drug-withdrawal scopolamine agent i.e., an injectable preparation of scopolamine hydrobromide subsided with chlorpromazine hydrochloride.

II. Discussion of the Prior Status

At present, various narcotics have been widely abused. Drug abuse is hazardous to this civilized society. Eutherapeutical drugs and their application are used for drug-withdrawal throughout the world. Nevertheless, in some countries, drug addicts are treated cruelly. They are arrested, sent to jail, isolated, forced to discontinue drug-intake and without any treatment while they intolerably suffer from abstinence syndromes. Drug-withdrawal without any treatment therefor refered to as 'Cold Turkey', which is neither medically approved nor under any approved regulatory provision. It has been widely adopted in many countries that opium addicts are advised to take a substitute like methadone, and to overcome the abstinence syndromes from drug-withdrawal by progressively reducing the dosage of the substitute.

1. Methadone maintenance regimen:

Methadone (a new kind of narcotic analgesic) was synthesized by two German scientists, Nockmuhl and Ehrhavf, to solve the shortage of morphine during World War II. It was first clinically adopted as a substitute for morphine in 1945 and put on sale in the USA in 1947. In 1955, methadone was used to suppress abstinence syndromes from drug-withdrawal of heroin, Since then, this method has adopted world-wide as an effective treatment for drug-withdrawal.

2. Methadone-clonidine for drug-withdrawal:

Clonidine, a nonopioid analgesic drug, was first proposed to be used for the withdrawal of heroin by the American scientists, Gold et al. in 1978. It has been therefor proven improve the drug-withdrawal effect of a methadone regimen.

3. Methadone-clonidine-propoxyphene for drug-withdrawal:

Propoxyphene is a synthetic substitute of morphine and similar to methadone in chemical structure. It is also a narcotic analgesic. It is inappropriate to use propoxyphene alone. The combined use of propoxyphene and methadone could improve the drug-withdrawal effect of a methadone maintenance regimen.

Another substitute like naloxone has also been used to ensure a methadone maintenance regimen but showed no beneficial effect when used alone. Although drug-withdrawal by narcotic a analgesic i.e. methadone maintenance subsided with clonidine, is widely considered to be effective, it possesses inevitable shortcomings of a long time course, high expense and drug dependence of its own. There has been a long search for drugs superior to that outlined above for use in drug-withdrawal.

SUMMARY OF THE INVENTION

The object of the invention is to provide a novel and rapid method for drug-withdrawal, and has been realized successfully with a compound agent of scopolamine subsided with chlorpromazine instead of narcotic analgesic e.g. opioid for patients in drug dependence.

Physical dependence and psychologic dependence can be produced from drug-abuse, and, upon discontinuance of drug intake, the abstinence syndromes which addicts have suffered intolerably are hard to overcome by the drug-withdrawal regimen mentioned above.

Enkephalin and endorphin are endogenous analgesic substances which are secreted at a baseline level to bind opiate receptors to produce a physiologic accommodation. Under stress, more endogenous analgesic substances are secreted to bind more opiate receptors so as to alleviate pain. Exogenous analgesic substances are usally needed to bind more opiate receptors in order to block the afferent irritable stimulus.

However, abuse of morphine-like substances or opioid may, through a feedback mechanism, result in secretory disturbance of nerves producing endogenous analgesic substances so that the exogenous analgesic substances play a decisive role in replacing the physiologic accommodation effect of endorphine especially its analgesic function. On the other hand, while promoting an analgesic effect, morphine-like substances can also substantiate cerebral cortex action, increase pulse transmission between cerebral cortex nerve cells and enhance transmission among these nerves, so that afferent signals from peripheral nerves are much enhanced and thus produce euphoria.

Meanwhile, the excessive use of exogenous morphine inhibits the secretion of endogenous analgesic substances such as dopamine and serotonin. Thus Ach plays a decisive role in abstinence syndromes such as overtension of smooth muscle, constipation and vomiting, etc. In addition, exogenous morphine competes against Ach for cholinergic receptor. Overdose morphine may cause congregation of Ach in synaptic vesicles of cholinergic nerves and interfere partially with the function of cholinergic nerves.

Accordingly, addicts who discontinue using morphine will produce abstinence syndromes that are characterized as follows:

a. In case of morphine, dependence, withdrawal of morphine while enkephalin is not yet secreted normally, may result in an abnormal decrease of pain-threshold so that some metabolic substances, which otherwise are not sensitive may cause pain, This is called hyperalgesia. For instance, intolerable pain may occur when lactic acid accumulates after exercise.

b. In the mean time, as a result of lack of competition by morphine-like substances, Ach accumulated in synaptic vesicle is increasingly released, and the abstinence syndrome appears.

c. As a result of morphine intake, some kinds of nerves cells are inhibitted in producing dopamine and/or 5-TH and are unable to recover in a short time so that they cannot antagonize Ach.

d. Decreasing stimulation of morphine at the cerebral cortex may cause addicts languid and yawning. The presence of dysphoria and dysthymiac is caused by the abnormally increased secretion of Ach.

The present invention concerns the preparation of a scopolamine agent for effective drug-withdrawal as to reduce abstinence syndrome rapidly. In addition, the agent has no dependence potential and is economic.

DETAILED DESCRIPTION OF THE INVENTION

The object of the present invention is to provide a novel drug-withdrawal scopolamine agent (DSA) which is an injectable preparation consisting of scopolamine hydrobromide as a main component and chlorpromazine hydrochloride as a subsidiary component.

The drug-withdrawal mechanism of scopolamine. Scopolamine hydrobromide is a muscarine-cholinergic antagonist, with a chemical structure a shown below:

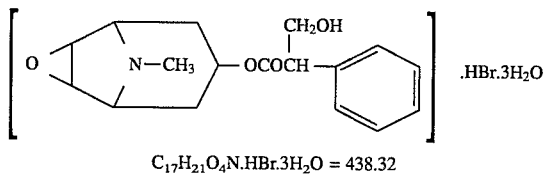

$C_{17}H_{21}O_4N.HBr.3H_2O = 438.32$

I. Scopolamine is an anticholinergic drug with inhibitory effect on M2-cholinergic receptors of excited type, it results in:

(1) inhibiting of the cerebral cortex, causing sedation and antivertigo:

(2) inhibiting the secretion of respiration tract and lacrimal gland:

(3) antispasm and analgesia:

(4) antiparkinsonism and platycoria.

II. Slight-anesthestic effect

Scopolamine has an inhibitory effect on the cerebral cortex i.e. slight-anesthetic effect, so drug addicts withdraw from a drug in drug-induced sleeping and abstinence syndromes decline without respiration system and blood circulation system disturbances.

III. Antagonist to the usual respiration-inhibiting effect of morphine and the like.

Scopolamine can stimulate the respiratory center, antagonizing the inhibitory action of morphine or pethidine.

IV. Promote the metabolism and excretion of morphine.

Subsidiary effects of small dose Chlorpromazine

Chlorpromazine hydrochloride is a transquilizer. Its chemical structure is shown below:

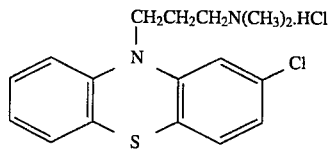

$C_{17}H_{19}N_2ClS.HCl = 355.30$

1. To antagonize the untoward-effects of scopolamine

Although scopolamine can stimulate the circulatory and respiratory center, it may cause convulsions as well as an elevation of body the temperature. In contrast, chlorpromazine has therapeutic effects such as sedation, antimania and decreasing body temperature, etc. To antagonize the untoward-effects of scopolamine, a small dose of chlorpromazine is enough in a drug withdrawal treatment.

2. Synergy in drug-induced sleeping

Scopolamine induces sleep by depressing M-cholinergic nerves in the cerebral cortex, while chlorpromazine functions by blocking the ascending subcortical CNS. The combination of scopolamine and chlorpromazine is synergic in drug-induced sleeping.

Chlorpromazine, both as a supressor of brain stem reticular formation and as a blocker for the transmission of the ascending activating system of the cerebral cortex, can subsidize scopolamine positively in drug induced sleeping. It can also partially antagonize the hyperfunction of Ach.

On the other hand, chlorpromazine exhibits a safeguard effect in the drug withdrawal, for the two drugs are antagonistic to one another in their untoward effects. For instance, chlorpromazine antagonizes scopolamine in tranquilizing the patients of their restlessness due to the overactivity of the subcortical system caused by scopolamine. On the other hand, chlorpromazine is antagonized in its inhibition of respiration and blood circulation by scopolamine. Therefore, scopolamine and chlorpromazine are antagonist to each other in untoward effects but are synergists in drug withdrawal.

The combined application of both drugs for drug withdrawal is both effective and safe.

This invention provides a sterile compound agent which consists of scopolamine as a main component and chlorpromazine hydrochloride as a subsidiary component. 2 ml of this agent contains 0.3–9 mg of scopolamine and 12.5–75 mg of chlorpromazine with adequate amount of stabilizer. Scopolamine hydrobromide and chlorpromazine hydrochloride can also be used in the form of separate injections.

1000 ml sterile compound injection of scopolamine and chlorpromazine agent consists of the following components:

| | |
|---|---|
| Scopolamine hydrobromide | 0.15–4.5 g |
| Chlorpromazine hydrochloride | 6.25–37.5 g |
| Sodium pyrosulfite | 2 g |
| Vitamin C | 2 g |
| EDTA | 0.1 g |
| Sodium chloride | 0.6 g |

Preparation procedure for the compound agent:

(1) dissolve all components of the drug withdrawal scopolamine agent (DSA) in $N_2$-saturated water for injection;

(2) homogenize the aqueous and add water (for injection) to nearly full volume;

(3) assay the partial-finished agent against a standard;

(4) adjust pH to 3.0–3.5, make up the partial-finished agent with water (for injection) to full volume;

(5) filter through a sintered glass filter #4 with filter membrane of 0.65 um pore size;

6) pour the transparent filtrate into a 2 ml-ampul, fill with nitrogen gas, seal the ampul and sterilize at 100° C. for 30 minutes.

The compound injection of scopolamine and chlorpromazine is used as a drug withdrawal agent in the withdrawal of heroin, opiate, 'huangpi' (a type of opiate), morphine, dolantin, fentanyl, qiantondini, dihydroetorphini, and/or alchohol as well.

This agent has been proved effective clinically through 512 drug withdrawal cases, of which 208 cases were analysed statistically. In the drug withdrawal treatment, the following criteria are used:

1. Criteria of diagnosis

According to DSM-III-R and Opiate Withdrawal Scale, criteria of abstinence syndrome, and course and grade of psychomotive substances (opiate) dependence were set up for the following five aspects, i.e. physiological, psychological, sexual, social behavioral and comment on drug abuse.

2. Criteria of drug withdrawal effect

After drug withdrawal with the scopolamine-chlorpromazine compound agent, (1) according to the Opiate Withdrawal Scale test, abstinence syndromes are remitted, social behavior is on the mend and drug dependence disappears;

(2) according the to Eysenck Personality Quiz, scores of lying and enigmatizing decrease, impulsion disappears and emotions are in a stable phase;

(3) according to the Laboratory Criterion, concentrations of morphine in plasma, corticosteroids, enkephalin and sexual hormones are within normal ranges and the immunological functions are normal;

(4) according to the Precipitation Test with naloxone, both physical and psychologic drug withdrawal are generally ensured.

The above cases are reported as below.

1. Cases classified according to the types of abused drugs

TABLE 1

Types and cases of drug abuse concerned

| Abused Drugs | Cases | Percentage(%) |
|---|---|---|
| Heroin(White powder IV) | 75 | 36.10 |
| 'Huangpi' (Yellow, indigenous opioid in northwestern China) | 85 | 40.86 |
| Dolantin injection(including those also using qiantondini and/or dihydroetorphini) | 44 | 21.12 |
| Dihydroetorphini | 4 | 1.92 |

2. Cases classified according to the dosage of abused drug

TABLE 2

Dosage of abused drug

| Abused Drugs | Dosage (g/day) | Cases | Persntage(%) |
|---|---|---|---|
| Heroin | less than 0.5 | 8 | 3.84 |
| (max. 5 g/day) | 0.5 to 1.0 | 30 | 14.40 |
|  | more than 1.0 | 37 | 17.70 |
| 'Huangpi' | less than 0.5 | 11 | 5.28 |
| (max. 8 g/day) | 0.5 to 1.0 | 35 | 16.96 |
|  | more than 1.0 | 39 | 18.72 |
| Dolantin | less than 0.2 | 7 | 3.36 |
| (max. 7 g/day) | 0.2 to 1.0 | 24 | 11.52 |
|  | more than 1.0 | 13 | 6.24 |
| Dihydroetorphini (max. 0.8 × $10^{-3}$ g/day) | less than 0.2 × $10^{-3}$ | 2 | 0.96 |
|  | more than 0.2 × $10^{-3}$ | 2 | 0.96 |

3. Cases classified clinically

According to the duration and dosage of drug abuse as well as the severity of the abstinence syndrome, the degree of drug dependence is classified as mild, medium and severe.

(1) Cases of mild degree of drug dependence

The duration of drug abuse is less than half of a year and dosage of the abused drug is less than 0.5 g/day. For these cases, only slight abstinence syndromes appear such as yawning, rhinorrhea and lacrimation.

(2) Cases of medium degree drug dependence

The duration of drug abuse is from half year to 2 years, and the dosage of abused drug is from 0.5 g/day to 1.0 g/day. Of medium degree, abstinence syndromes appear such as yawning, lacrimation, chest pain, restlessness, chilliness, arthralgia and hip pain.

(3) Cases of severe degree drug dependence

The duration of drug abuse is more than 2 years and the dosage of abused drug is more than 1.0 g/day. In addition to those syndromes listed in the medium degree category, severe abstinence syndromes such as nausea, vomiting, abdominal pain, muscule pain, diarrhea, perspiration, bradysphygmia and decreased blood pressure also appear.

4. Drug withdrawal regimen

Patients were divided into four groups. Each group received one type of remedy for drug withdrawal for 3 days. If patients in group II or group III exhibited little therapeutical effect after 3 days of drug withdrawal, they were treated with the invented DSA.

Group I: Intravenous drip or intravenous injection of 0.3–9.0 mg scopolamine and 12.5–75 mg chlorpromazine. Supplemented with 20 mg diazepan if the patients were still restless.

Group II: Intravenous drip or intravenous injection of 40–60 mg anisodamine and 12.5–75 mg chlorpromazine hydrochloride. Supplemented with 20 mg of diazepan if the patients were still restless.

Group III: Intravenous drip or intravenous injection of 50–75 mg chlorpromazine. Supplemented with 20 mg diazepan if the patients were still restless.

Group IV: Methadone maintenance for 21 days. During the first 5 days of the regimen, 30–40 mg methadone was given in the first day and then decreased in steps of 20% day-by-day thereafter, Five days later, the dosage was further reduced by 1.0 mg in each following day until the 21st day.

Patients in each group fasted for 4–6 hours before withdrawal treatment. During the course of treatment, food-intake, vomiting and diarrhea of the patients were observed so as to take timely action in case of water-electrolyte inbalance. If necessary, compound of amino acid, albumin and plasma etc. are supplied. Where high fever and/or infection were observed, antipyretic, corticosteroid and/or antibiotic should be used in time. Hemostasis or blood transfusion was ready in case of hemorrhage of gastrointestinal tract.

Besides pharmacotherapy, psychotherapy had been offered until the withdrawal treatment was completed. For instance, individual psychotherapy aimed at helping the patient to understand his fundamental problems should be administered, and the patients are expected to benefit from the treatment.

The withdrawal treatment was divided into two phases i.e. 3 days of intensive withdrawal treatment followed by 5 days of rehabilitative treatment.

(1) Intensive drug withdrawal treatment

Patients were quite different in drug dependence. Some of them had already discontinued drug abuse for a while before arriving to get withdrawal treatment and before signs of any abstinence syndrome appeared. The others still taking 'drug' hid before treatment. For the former, withdrawal treatment with DSA was given immediately, and a therapeutic effect occurred within 3 days of uninterrupted treatment. For the latter, intravenous injection of 0.4–0.8 mg naloxon to antagonize morphine-like substances in vivo until the patients' abstinence syndrome appeared. Then the same treatment was offered as described.

50 patients were randomly chosen for Group II and Group III with 25 patients in each group. Both groups received withdrawal treatment with other kinds of therapeutic drugs for 3 days when their abstinence syndromes were observed. Therapeutic effects of each group are listed below.

TABLE III

The effects of withdrawal treatment
(DSA vs other kinds of drugs for withdrawal treatment)

| Items[1] | Drugs for withdrawal treatment[2,3,4,6] | | | |
|---|---|---|---|---|
|  | DSA | C1 | C2 | C3 |
| 1 | 5' | 20' | 22' | 21day |
| 2 | 3'–10' | 15'–30' | 15'–32' |  |
| 3 | 85% | 50% | 35% | 0% (unrecovered) |

TABLE III-continued

The effects of withdrawal treatment
(DSA vs other kinds of drugs for withdrawal treatment)

| Items[1] | Drugs for withdrawal treatment[2,3,4,6] | | | |
|---|---|---|---|---|
| | DSA | C1 | C2 | C3 |
| 4 | 80% | 23% | 10% | 0% (unrecovered) |
| 5 | 91% | 57% | 47% | 0% (PAS)[5] |

Notes:
[1]Items:
1. average time for eliminating abstinence syndromes;
2. ranges of the time in Item-1;
3. recovery rate of normal living style(food-intake, defecation and sleeping);
4. mental and physical recovery rate;
5. physical dependence (or abstinence syndromes) remission rate.
[2]Drugs for withdrawal treatment:
DSA: Drug-withdrawal Scopolamine Agent
C1: 654-2(anisodamine) + chlorpromazine;
C2: chlorpromazine;
C3: methadone
[3]Intravenous injections (with exception of methadone) were used to remit abstinence syndromes.
[4]Records of abstinence syndromes had been taken for each group except Item-5 was set for groups with DSA, C1 and C2 on the 3rd day and for the group with methadone maintenance on the 21st day.
[5]PAS: Persisted Abstinence Syndromes.
[6]For groups except methadone maintenance, $P < 0.01$.

Table III illustrates that the withdrawal treatment effect of DSA is significantly better than that of 654-2(anisodamine)-chlorpromazine or chlorpromazine.

(2) Rehabilitative treatment

A rehabilitative treatment had been given for 5–7 days after 3 days of intensive drug withdrawal with DSA when most of the patients had their abstinence syndromes alleviated. Only two patients of the group having a severe degree of drug dependence, still complained to be uncomfortable with chest pain and/or pain over whole body. Meanwhile, only half of the patients of the groups having mild or medium degrees of drug dependence had their abstinence syndromes controlled. For the purpose of complete drug withdrawal, a rehabilitative treatment is necessary to eliminate morphine and its metabolites from the patients' bodies. According to the determination of morphine concentration in plasma during drug withdrawal, 7–8 days of rehabilitative treatment are required. 5–8 tablets of Delishu (each tablet contains 0.09 mg of 654-2) were administered three times a day, and the intravenous dripping or intravenous injection of 20–40 mg Anlishu (each ampul contains 20 mg of 654-2) was given twice a day to adjuvant scopolamine in the drug withdrawal. A substantial concentration of scopolamine should be maintained in the blood during the treatment.

Nevertheless, like the intensive drug withdrawal treatment, symptomatic treatment, supportive treatment and psychological treatment should be instituted during the period of rehabilitative treatment, so the patients could be rehabilitated well.

Classification of the drug-withdrawal effects (1) Complete drug withdrawal

Physical dependence is eliminated as abstinence syndrome has been completely remitted. Sleeping, food-intake and defecation have recovered to a normal condition. No abstinence syndrome appears after the intravenous injection of 0.4–0.8 mg of naloxon (precipitation test).

(2) Partial drug withdrawal

Physical dependence is basically eliminated as major abstinence syndrome disappears. Normal living state has basically recovered. Nevertheless, chilliness, restlessness, yawning, lacrimation, abdominal pain and insomnia appeared at a time but were mild. Abstinence syndromes appeared but were slight and short in duration during the precipitation test.

(3) Drug withdrawal failure

Physical dependence was not eliminated and abstinence syndromes were uncontrolled.

Statistical results of the three day intensive drug withdrawal treatment with DSA are given in Table IV.

TABLE IV

The effects of the intensive drug withdrawal treatment with DSA

| Drug dependence degree | Number of cases | % | Complete | % | Partial | % | Failure |
|---|---|---|---|---|---|---|---|
| Mild | 46 | 22.6 | 46 | 100 | 0 | 0 | 0 |
| Medium | 110 | 72.4 | 110 | 100 | 0 | 0 | 0 |
| Severe | 52 | 25 | 37 | 71 | 15 | 29 | 0 |
| Total | 208 | 100 | 193 | 92.8 | 15 | 7.2 | 0 |

6. Clinical observation (1) Drug-induced sleeping. Generally, after the first injection of DSA, patients fell asleep within 3–5 minutes even within 2.5 minutes. Sleeping was verified when no response was observed to the calling test. As soon as the patients had been in drug-induced sleeping, they did not suffer from abstinence syndrome.

(2) Vital signs a. Body temperature: As a result of seasonal change, body temperature may be 0.5°–1.0° C. higher in summer than in other seasons. Patients with body temperature over 38.5° C. were considered to have fever and were antipryeted. Patients with body temperature increasing less than 1° C. were treated by physical cooling, the fever generally subsided after drug degradation.

b. Blood pressure: During treatment, systolic blood pressure slightly elevated by 1.33–5.32 KPa (10–40 mmHg) or 2.66 KPa (20 mmHg) on average.

c. Heart rate and rhythum: Patients' heart rates increased by 20–60/min or 30/min on average. Many drug abusers within the severe drug dependence group had arrhythm (extrasystol) before treatment and it disappeared after treatment with DSA.

d. Respiration: Scopolamine is also a strong respiration stimulant. 1 mg scopolamine antagonizes 20 mg morphine. During treatment, the frequency of respiration increased by 8–20/min or 12/min on average and the depth of respiration also increased. When respiration was stimulated, relapse of prebase may occur to block ventilation and should be watched.

e. Pupil: Treatment with DSA may cause platycoria by 2–4 mm in all cases.

(3) Other signs

Facial flushing, raving, restlessness, perspiration and sensations of warmth in the limbs are clinical signs indicating the maximum permissible dose of scopolamine.

(4) Side effects

Enuresis usually happened while the patients were in DSA-induced sleeping.

Vomiting was likely to appear several minutes after the injection of DSA and frequently lasted as long as 3 days. Diarrhea occured after drug withdrawal with DSA for 3 days. Scopolamine can promote gastrointestinal peristalsis and thus diarrhea occurred at the beginning of gastrointestinal hyper-peristalsis. On awakening from the DSA-induced sleeping, patients were likely in confusional a state and even manifested behavior disorders. These patients were monitered carefully.

(5) Duration of DSA-induced sleeping

Scopolamine metabolism lasted 4–6 hours. Having been sleeping for 2–6 hours on the average, patients were about to wake and were completely lucid in 4–12 hours or 8 hours on the average.

7. Concentration of morphine in plasma and urine

A concentration of free-morphine in plasma was detected for opiate (including heroin and/or "Huangpi" etc.) abusers with HPLC determination (using an instrument made by Waters). Before drug withdrawal with DSA, free-morphine as high as 0.8 μg/ml(800 ng/ml) in plasma of heroin abusers was detected and decreased to 40 ng/ml 7–8 days later after the drug withdrawal when no abstinence syndrome was observed.

Moreover, the concentration of integrated morphine (free-morphine and conjugated morphine) in urine was determined in 25 cases by radioimmunoassay autoanalyzer. The range of 1616 ng/ml-446 μg/ml for opiate patients before treatment was observed that of a normal person should be less than 10.0 ng/ml. By this means, it was routinely checked as to whether the patients were concealing their addiction to opiate during the withdrawal treatment.

8. Observation of immunological function and sexual function

The inventor discovered that heroin abusers usually had sexual disorder eg. frigidity and sexual impotence etc. They had low concentration of testosterone and estradiol in their blood serum before treatment and had notably higher concentrations after treatment with DSA for 7 days. This indicated that drug abusers recovered also in their sexual function after treatment with DSA. Immunological function test showed that drug abusers had immunological deficiency and recovered as the concentration of C3 returned to normal after the treatment.

Another test indicated that the concentration of Fn in blood serum of drug abusers was obviously low. The longer the duration of drug abuse and the larger the dosage of abused drug, the lower the concentration of Fn the level. Fn recovered after treatment with DSA for 8 days.

9. Auto-controlled personality test by Eysenck Personality Quiz before and after withdrawal treatment with DSA Scores of lying and enigmatizing of addicts were higher than that of normal person and were obviously lower after treatment. The scores in other dimensions of the test also changed obviously before and after treatment. Therefore, it is concluded that patients regained their mental health from the withdrawal treatment while their abstinence syndromes were remitted by DSA.

T scores in different dimensions of EPQ in drug abusers before and after withdrawal treatment with DSA ($\bar{X} \pm SD$)

| Dimension | Before treatment | After treatment | P |
|---|---|---|---|
| L | 55.23 ± 10.51 | 50.34 ± 10.02 | <0.01 |
| E | 50.80 ± 11.67 | 54.66 ± 10.85 | <0.05 |
| N | 55.57 ± 11.01 | 58.64 ± 10.02 | <0.05 |
| P | 52.73 ± 11.54 | 56.36 ± 11.53 | <0.05 |

According to clinical observation and communication with the patients, most patients commented that they had no more intention to abuse drug again after treatment with DSA for 3–5 days. Moreover, some of the patients even felt averse to the drugs they had abused. Most of the patients who had been in drug dependence were drug-withdrawn and went home after the withdrawal treatment with the invented DSA for 7–8 days, Nevertheless, there were a few who not only were suffering seriously in drug dependence but also had other diseases, especially those patients who suffered from hepatomegalia or extensive weakness because of an alimentary dysfunction, and had a rather slow recovery of their physical and mental damage. For these patients, course of treatment should be prolonged to about 15 days.

According to the classification of complete drug withdrawal and the precipitation test with naloxon, the success rate of the withdrawal treatment with DSA is as follows.

(1) 100% abstinence syndrome remitted.

(2) 100% physical dependence eliminated.

(3) 100% safe guarded throughout the treatment.

No drug withdrawal failure had ever happened since the first case was treated with DSA.

Preparation Example 1: Preparation of Compound an Injectable Preparation of a Compound Scopolamine-Chlorpromazine for Drug Withdrawal 1. Standard Agent for injection. 2 ml of the sterile agent contains 0.3 mg scopolamine hydrobromide and 12.5 mg chlorpromazine hydrochloride. (Concentration of main drugs shall be in the range of 90–110% as much as stated on the label.)

2. Description

A colorless or almost colorless, transparent liquid, pH=3.0–3.5.

3. Prescription 1000 ml of the agent consists of:

| | |
|---|---|
| Scopolamine hydrobromide | 0.15 g |
| Chlorpromazine hydrochloride | 6.25 g |
| Sodium pyrosulfite | 2 g |
| Vitamin C | 2 g |
| EDTA | 0.1 g |
| Sodium chloride | 0.6 g |
| Water for injection | make up to 1000 ml |

4. Technique (1) weigh accurately the components described in the prescription and dissolve them in $N_2$-saturated water for injection;

(2) homogenize the solution and make up with water for injection to nearly full volume;

(3) assay the partially-finished agent against standard;

(4) adjust pH to 3.0–3.5, make up with water for injection to full volume;

(5) filter through a sintered glass filter #4 with filter membrane of 0.65 um pore size;

(6) pour the transparent filtrate into a 2 ml-ampule, fill with nitrogen gas, seal the ampule and sterilize at 100° C. for 30 minutes.

The agent should be stored in a cool place, protected from light.

The agent is an irritant to skin and mucosa and may cause mydriasis. During preparation, the pharmacists are advised to put on rubber gloves and protective glasses. and to stop handling the agent in case mucositis occurs.

Preparation Example 2: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 0.6 mg scopolamine hydrobromide and 12.5 mg chlorpromazine hydrochloride. (Concentration of the main drugs shall be in the range of 90–110% as much as stated on the label.)

Prescription:
1000 ml of the agent consists of:

| | |
|---|---|
| Scopolamine hydrobromide | 0.30 g |
| Chlorpromazine hydrochloride | 6.25 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 3: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 0.9 mg scopolamine hydrobromide and 25 mg chlorpromazine hydrochloride. (Concentration of the main drugs shall be in the range of 90–110% as much as stated on the label.)

Prescription:
1000 ml of the agent consists of:

| | |
|---|---|
| Scopolamine hydrobromide | 0.45 g |
| Chlorpromazine hydrochloride | 12.5 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 4: Preparation of an Injection Preparation of a Compound of Scopolamine-Chlorpromazine for Drug Withdrawal Technique of preparation and description of the agent are the same as described in Preparation Example 1.

Standard: 2 ml of the sterile agent contains 1.2 mg scopolamine hydrobromide and 25 mg chlorpromazine hydrochloride. (Concentration of the main drugs shall be in the range of 90–110% as much as stated on the label.)

Prescription:
1000 ml of the agent consists of:

| | |
|---|---|
| Scopolamine hydrobromide | 0.60 g |
| Chlorpromazine hydrochloride | 12.5 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 5: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 1.5 mg scopolamine hydrobromide and 25 mg chlorpromazine hydrochloride. (Concentration of the main drugs shall be in the range of 90–110% as much as stated on the label.)

Prescription:
1000 ml of the agent consists of:

| | |
|---|---|
| Scopolamine hydrobromide | 0.75 g |
| Chlorpromazine hydrochloride | 12.5 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 6: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 1.8 mg scopolamine hydrobromide and 25 mg chlorpromazine hydrochloride. (Concentration of the main drugs shall be in the range of 90–110% as much as stated on the label.)

Prescription:
1000 ml of the agent consists of:

| | |
|---|---|
| Scopolamine hydrobromide | 0.90 g |
| Chlorpromazine hydrochloride | 12.5 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 7: Preparation of an Injection Preparation of a Compound of Scopolamine-Chlorpromazine for Drug Withdrawal Technique of preparation and description of the agent are the same as described in Preparation Example 1.

Standard: 2 ml of the sterile agent contains 2.1 mg scopolamine hydrobromide and 25 mg chlorpromazine hydrochloride. (Concentration of the main drugs shall be in the range of 90–110% as much as stated on the label.)

Prescription:
1000 ml of the agent consists of:

| | |
|---|---|
| Scopolamine hydrobromide | 1.05 g |
| Chlorpromazine hydrochloride | 12.5 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 8: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 2.4 mg scopolamine hydrobromide and 25 mg chlorpromazine hydrochloride. (Concentration of the main drugs shall be in the range of 90–110% as much as stated on the label.)

Prescription:
1000 ml of the agent consists of:

| | |
|---|---|
| Scopolamine hydrobromide | 1.20 g |
| Chlorpromazine hydrochloride | 12.5 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 9: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 2.7 mg scopolamine hydrobromide and 25 mg chlorpromazine hydrochloride. (Concentration of the main drugs shall be in the range of 90–110% as much as stated on the label.)

Prescription:
1000 ml of the agent consists of:

| | |
|---|---|
| Scopolamine hydrobromide | 1.35 g |
| Chlorpromazine hydrochloride | 12.5 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 10: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 3.0 mg scopolamine hydrobromide and 50 mg chlorpromazine hydrochloride. (Concentration of the main drugs shall be in the range of 90–110% as much as stated on the label.)

Prescription:
1000 ml of the agent consists of:

| | |
|---|---|
| Scopolamine hydrobromide | 1.50 g |
| Chlorpromazine hydrochloride | 25 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 11: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 3.5 mg scopolamine hydrobromide and 50 mg chlorpromazine hydrochloride. (Concentration of the main drugs shall be in the range of 90–110% as much as stated on the label.)

Prescription:
1000 ml of the agent consists of:

| | |
|---|---|
| copolamine hydrobromide | 1.75 g |
| Chlorpromazine hydrochloride | 25 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 12: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 4.0 mg scopolamine hydrobromide and 50 mg chlorpromazine hydrochloride. (Concentration of the main drugs shall be in the range of 90–110% as much as stated on the label.)

Prescription:
1000 ml of the agent consists of:

| | |
|---|---|
| Scopolamine hydrobromide | 2.0 g |
| Chlorpromazine hydrochloride | 25 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 13: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 4.5 mg scopolamine hydrobromide and 50 mg chlorpromazine hydrochloride. (Concentration of the main drugs shall be in the range of 90–110% as much as stated on the label.)

Prescription:
1000 ml of the agent consists of:

| | |
|---|---|
| Scopolamine hydrobromide | 2.25 g |
| Chlorpromazine hydrochloride | 25 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 14: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 5.0 mg scopolamine hydrobromide and 50 mg chlorpromazine hydrochloride. (Concentration of the main drugs shall be in the range of 90–110% as much as stated on the label.)

Prescription:
1000 ml of the agent consists of:

| | |
|---|---|
| Scopolamine hydrobromide | 2.50 g |
| Chlorpromazine hydrochloride | 25 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 15: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 5.5 mg scopolamine hydrobromide and 50 mg chlorpromazine hydrochloride. (Concentration of the main drugs shall be in the range of 90–110% as much as stated on the label.)

Prescription:
1000 ml of the agent consists of:

| | |
|---|---|
| Scopolamine hydrobromide | 2.75 g |
| Chlorpromazine hydrochloride | 25 g |
| Sodium pyrosulfite | 2 g |
| Vitamin C | 2 g |
| EDTA | 0.1 g |

-continued

| | |
|---|---|
| Sodium chloride | 0.6 g |
| Water for injection | make up to 1000 ml |

Preparation Example 16: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 6.0 mg scopolamine hydrobromide and 50 mg chlorpromazine hydrochloride. (Concentration of the main drugs shall be in the range of 90–110% as much as stated on the label.)

Prescription:

1000 ml of the agent consists of:

| | |
|---|---|
| Scopolamine hydrobromide | 3.0 g |
| Chlorpromazine hydrochloride | 25 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 17: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 6.5 mg scopolamine hydrobromide and 50 mg chlorpromazine hydrochloride. (Concentration of the main drugs shall be in the range of 90–110% as much as stated on the label.)

Prescription:

1000 ml of the agent consists of:

| | |
|---|---|
| Scopolamine hydrobromide | 3.25 g |
| Chlorpromazine hydrochloride | 25 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 18: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 7.0 mg scopolamine hydrobromide and 50 mg chlorpromazine hydrochloride. (Concentration of the main drugs shall be in the range of 90–110% as much as stated on the label.)

Prescription:

1000 ml of the agent consists of of:

| | |
|---|---|
| Scopolamine hydrobromide | 3.50 g |
| Chlorpromazine hydrochloride | 25 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 19: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 7.5 mg scopolamine hydrobromide and 50 mg chlorpromazine hydrochloride. (Concentration of the main drugs shall be in the range of 90–110% as much as stated on the label.)

Prescription:

1000 ml of the agent consists of:

| | |
|---|---|
| Scopolamine hydrobromide | 3.75 g |
| Chlorpromazine hydrochloride | 25 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 20: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 8.0 mg scopolamine hydrobromide and 75 mg chlorpromazine hydrochloride. (Concentration of the main drugs shall be in the range of 90–110% as much as stated on the label.)

Prescription:

1000 ml of the agent consists of:

| | |
|---|---|
| Scopolamine hydrobromide | 4.0 g |
| Chlorpromazine hydrochloride | 37.5 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 21: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 8.5 mg scopolamine hydrobromide and 75 mg chlorpromazine hydrochloride. (Concentration of the main drugs shall be in the range of 90–110% as much as stated on the label.)

Prescription:

1000 ml of the agent consists of:

| | |
|---|---|
| Scopolamine hydrobromide | 4.25 g |
| Chlorpromazine hydrochloride | 37.5 g |
| Sodium pyrosulfite | 2 g |
| Vitamin C | 2 g |
| EDTA | 0.1 g |
| Sodium chloride | 0.6 g |
| Water for injection | make up to 1000 ml |

Preparation Example 22: Preparation of an Injectable Preparation of a Compound of Scopolamine-Chlorpromazine for Drug Withdrawal Technique of preparation and description of the agent are the same as described in Preparation Example 1.

Standard: 2 ml of the sterile agent contains 9.0 mg scopolamine hydrobromide and 75 mg chlorpromazine hydrochloride. (Concentration of the main drugs shall be in the range of 90–110% as much as stated on th label.)

Prescription:
1000 ml of the agent consists of:

| | |
|---|---|
| Scopolamine hydrobromide | 4.50 g |
| Chlorpromazine hydrochloride | 37.5 g |
| Sodium pyrosulfite | 2 g |
| Vitamin C | 2 g |
| EDTA | 0.1 g |
| Sodium chloride | 0.6 g |
| Water for injection | make up to 1000 ml |

Examples of Case Report

Example 1: Drug Withdrawal for Heroin Addiction

Liang, male, 38 years old, from Guangzhou. The patient had been using heroin up to 0.3 g/dose 3–4 times daily for half a year. In the withdrawal from heroin, signs of abstinence syndrome included yawning, lacrimation, chilliness, gooseflesh, dejection and chest pain. Body temperature, blood pressure, pulse rate and respiration rate were normal. The liver was palpated 2 cm below the xiphisternum. The patient was offered treatment with DSA on the day of admission, and 3 days later, mental health resumed with normal food-intake and excrement. He recovered completely after treatment with DSA for given 4 times and was discharged 5 days later.

Example 2: Drug Withdrawal for 'Huangpi' Addiction

Zhang, male, 28 years old, from Tongguan in Shanxi province. The patient had been using 'Huangpi' up to 2 g/dose 5–6 times daily for 4 years, he had made 10 attempts to withdraw from the drug but in vain. Abstinence syndromes: yawning, rhinorrhea, lacrimation, anxiety, short breath, chilliness, gooseflesh, insomnia, abdominal pain, arthralgia, restlessness, perspiration, diarrhea and chilliness in the limbs. Body temperature, blood pressure, pulse rate and respiration rate were normal, but his features looked emaciated, while the tongue was covered with black-yellowish fur. Heart auscultation revealed ventricular prematures, and hepatomegalia 1.5 cm below xiphisternum. He was treated with DSA as soon as he was admitted while his abstinence syndromes appeared. He fell asleep 5 minutes after and became restless 15 minutes later with facial flushing and warmed-up limbs, and basic vital signs appeared to be in an exciting state 30 minutes later. He slept calmly with no more DSA given over the night. He was offered DSA injection for 8 times until the 9th day after admission, the abstinence syndrome disappeared with negative precipitation test result, and was discharged.

Example 3: Drug Withdrawal for Dolantin Addiction

Liu, male, 30 years old, from Taiyuan in Shanxi province. To alleviate nerves and headache, he had been using dolantin up to 100–500 mg/dose 1–2 times daily and subsided with qiantondini up to 100 mg/dose daily. At a reduced intake of these drugs, he felt short of breath, anxiety, insomnia and abdominal distension, although blood pressure, heart rate, respiration rate and body temperature were normal. He received DSA immediately after admission. The patient fell asleep 3 minutes after, his face became flushed and limbs warmed-up 15 minutes later. His mental state and appetite recovered on the 2nd day and he slept normally on the 3rd day. DSA injections were given 3 times and he was discharged on the 6th day.

Example 4: Drug Withdrawal for Qiantondini Addiction

Guo, male, 40 years old, from Dongyan in Zhejiang province. After the amputation of both legs, he took dolantin and qiantondini to alleviate his right stump neuralgia. The patient had been using qiantondini up to 200 mg/dose 4 times daily for 15 years. Withdrawal of the drug resulted in palpitations, restlessness, insomnia, and particularly severe stump neuralgia. His blood pressure, body temperature, heart rate and respiration were normal, but the tongue looked white and greasy. The patient was offered treatment with DSA on the day of admission. Food-intake and mental state recovered on the 2nd day, excrement improved on the 3rd day, and the patient only suffered from slight stump neuralgia on the 8th day when DSA was discontinued. He was discharged on the 11st day after rehabilitative treatment for 3 days.

Example 5: Drug Withdrawal for Dihydroetorphini Addiction

Wu, male, 20 years old, from Qunming in Yunnan province. After one year of heroin addiction, the patient received a withdrawal treatment with dihydroetorphini in a Withdrawal Setup in Qunming, southern China. He took 1–3 tablets of dihydroetorphini (40 ug dihydroetorphini in each tablet) dissolved in a liquid medium for injection each day and up to 30–40 tablets each day 4 months later. Abstinence syndromes included yawning, lacrimation. Shortness of breath, chilliness, insomnia, vomiting, abdominal pain, diarrhea and dysphoria etc. Temperature, blood pressure, heart rate and respiration rate remained normal, but the tongue looked yellowish black and hepatomegalia 4 cm below xiphisternum or 1.5 cm below ribs were palpated. He was offered treatment with DSA on the day of admission, The patient fell asleep 5 minutes after the injection, his face became flushed and his limbs warmed-up accompanied by restlessness and perspiration. On the 2nd day, he began to drink and take food, and the abstinence syndrome disappeared. On the 3rd day, his mental state and appetite were on the mend. He had received an injection of DSA 4 times until he was discharged in complete drug withdrawal on the 7th day following a rehabilitative treatment on the 6th day.

Example 6: Drug Withdrawal for Alchohol Addiction

Sigu, male, 44 years old from Hailaer in Inner Mongolia. He had abused alchohol for ten years. When drunk, he was an attacker and committed sabotage. He was forgetful, weak at calculation and not competent to any job, He was admitted as a patient having an alcohol dependence.

On examination, he had facial capillarectasia, hepatomegalia to 0.5 cm below xiphisternum, amnesia and a poor appetite.

After treatment with DSA 3 times, his mental state as well as memory improved with no desire for alcohol. He was given DSA 4 times during an eight-day treatment course, and was then discharged in high spirits.

The DSA of the present invention is a an injectable preparation of a compound of scopolaminehydrobromide and chlorpromazine hydrochloride for use in drug withdrawal. Each of the drugs may also be used in combination in separated injections for a drug withdrawal treatment.

What is claimed is:

1. A drug-withdrawal agent, comprising effective therapeutic amounts of scopolamine hydrobromide at about 0.5–4.5 mg/ml and chlorpromazine hydrochloride at about 6.25–37.5 mg/ml for treatment of opiate withdrawal.

2. The drug-withdrawal agent according to claim 1, in combination with an aqueous carrier.

3. The drug-withdrawal agent according to claim 2, comprising an effective amount of a stabilizing agent.

4. The drug-withdrawal agent according to claim 3, comprising about 6.25 mg/ml chlorpromazine hydrochloride and about 0.5–0.9 mg/ml scopolamine hydrobromide.

5. The drug-withdrawal agent according to claim 3, comprising about 12.5 mg/ml chlorpromazine hydrochloride and about 0.5–1.35 mg/ml scopolamine hydrobromide.

6. The drug-withdrawal agent according to claim 3, comprising about 25 mg/ml chlorpromazine hydrochloride and about 1.5–3.75 mg/ml scopolamine hydrobromide.

7. The drug-withdrawal agent according to claim 3, comprising about 37.5 mg/ml chlorpromazine hydrochloride and about 4–4.5 mg/ml scopolamine hydrobromide.

8. A drug-withdrawal agent, consisting essentially of an aqueous solution of:
   (a) about 0.5–4.5 mg/ml scopolamine hydrobromide;
   (b) about 6.25–37.5 mg/ml chlorpromazine hydrochloride;
   (c) about 2 mg/ml sodium pyrosulfite;
   (d) about 2 mg/ml vitamin C;
   (e) about 0.1 mg/ml EDTA; and
   (f) about 0.6 mg/ml sodium chloride.

9. A method for preparing a drug-withdrawal agent, comprising:
   (a) dissolving effective therapeutic amounts of scopolamine hydrobromide at about 0.5–4.5 mg/ml and chlorpromazine hydrochloride at about 6.25–37.5 mg/ml in water to provide a homogenous solution;
   (b) adjusting the solution to about pH 3.0–3.5; and
   (c) filtering the solution to provide the drug-withdrawal agent as a clarified solution.

10. The method according to claim 9, wherein the water in step (a) is $N_2$-saturated and suitable for injection.

11. The method according to claim 9, wherein the solution in step (c) is filtered through sintered glass filter with a filter membrane having an about 0.65 μm pore size.

12. The method according to claim 9, further comprising:
   (e) placing the clarified solution of the drug-withdrawal agent in sealed means for sterile containment of the solution; and
   (f) sterilizing the solution in the sealed containing means.

13. A method of assisting a patient in withdrawal from an opiate drug, comprising:
   administering to the patient an effective therapeutic amount of the drug-withdrawal agent of claim 1 to assist the patient in withdrawing from dependence on the opiate drug.

14. The method according to claim 13, wherein the drug is selected from the group consisting of heroin, opiates, huangpi, morphine, dolantin, fentanyl, giantondini, dihydroetorphini, and any combination thereof.

15. The method according to claim 13, wherein the drug-withdrawal agent is administered to the patient as an aqueous injection.

16. A method of assisting a patient in withdrawal from an opiate drug, comprising:
   administering to the patient an effective therapeutic amount of a drug-withdrawal agent by injecting a first aqueous solution comprising a therapeutically-effective amount of scopolamine hydrobromide of about 0.5–4.5 mg/ml and a second aqueous solution comprising a therapeutically-effective amount of chlorpromazine hydrochloride of about 6.25–50 mg/ml; the first and second solutions being administered in one or more injections;
   the combination of the first and second solutions being effective to assist the patient in withdrawing from dependence on the opiate drug.

17. The method according to claim 16, wherein the patient is administered the first solution as a 1-ml unit comprising about 0.5–0.9 mg/ml scopolamine hydrobromide, and the second solution as a 1-ml unit comprising about 25–50 mg/ml chlorpromazine hydrochloride.

* * * * *